US010551344B2

(12) United States Patent
Nishida

(10) Patent No.: US 10,551,344 B2
(45) Date of Patent: Feb. 4, 2020

(54) METHOD AND CIRCUIT FOR PROVIDING AN ACCURATE VOLTAGE FOR ELECTROCHEMICAL SENSING

(71) Applicant: AGENCY FOR SCIENCE, TECHNOLOGY AND RESEARCH, Singapore (SG)

(72) Inventor: Yoshio Nishida, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 15/557,458

(22) PCT Filed: Mar. 11, 2016

(86) PCT No.: PCT/SG2016/050115
§ 371 (c)(1),
(2) Date: Sep. 11, 2017

(87) PCT Pub. No.: WO2016/144266
PCT Pub. Date: Sep. 15, 2016

(65) Prior Publication Data
US 2018/0059054 A1 Mar. 1, 2018

(30) Foreign Application Priority Data
Mar. 11, 2015 (SG) .................. 10201501871 U

(51) Int. Cl.
*G01N 27/416* (2006.01)
(52) U.S. Cl.
CPC ................ *G01N 27/4163* (2013.01)
(58) Field of Classification Search
CPC ............. G01N 27/416; G01N 27/4162; F02D 41/1483; F02D 41/1461; F02D 41/1474;
(Continued)

(56) References Cited

U.S. PATENT DOCUMENTS

| 4,642,172 A | 2/1987 | Fruhwald |
| 5,198,771 A | 3/1993 | Fidler et al. |

(Continued)

OTHER PUBLICATIONS

PCT International Search Report for PCT Counterpart Application No. PCT/SG2016/050115, 5 pgs. (dated Apr. 27, 2016).
(Continued)

*Primary Examiner* — Eli S Mekhlin
(74) *Attorney, Agent, or Firm* — Womble Bond Dickinson (US) LLP

(57) ABSTRACT

A method and devices for controlling a potentiostat control loop circuit to provide an accurate cell voltage for electrochemically sensing a sample, wherein the cell voltage corresponds to a difference between electrode voltages a working electrode and a reference electrode of a three-electrode potentiostat are provided. The devices include a potentiostat control loop circuit having a first amplifier with an output connected to a counter electrode of the three electrode potentiostat and a first input connected to a first potential and a first switched capacitor network including a first capacitance device having a first electrode connected to a second input of the first amplifier. The first switched capacitor network is also operatively connected to the first amplifier for operating in a first mode and a second mode t switchably couple the second input of the first amplifier to the reference electrode of the three-electrode potentiostat. The method includes the step of, in the second mode, coupling the second input of the first amplifier to the reference electrode of the three-electrode potentiostat via the first capacitance device by coupling a second electrode of the first capacitance device to the reference electrode of the three-electrode potentiostat.

12 Claims, 8 Drawing Sheets

(58) Field of Classification Search
CPC ............... F02D 41/146; F02D 41/1455; F02D 41/1495; F02D 41/1496; F02D 41/1494; F02D 41/1444; F02D 41/30; Y10T 29/49002; Y10T 29/49155; Y10T 29/49114; Y10T 29/49128; Y10T 29/4921; Y10T 29/49126; Y10T 29/49794
See application file for complete search history.

(56) References Cited

U.S. PATENT DOCUMENTS

| | | | |
|---|---|---|---|
| 5,557,234 | A | 9/1996 | Collins |
| 6,275,094 | B1 | 8/2001 | Cranford, Jr. et al. |
| 7,924,062 | B2 | 4/2011 | Chiu |
| 8,018,281 | B2 | 9/2011 | Hasler et al. |
| 8,344,798 | B2 | 1/2013 | Garrity |
| 8,400,337 | B1 | 3/2013 | Xu et al. |
| 2008/0223719 | A1 | 9/2008 | Tam |
| 2013/0289522 | A1 | 10/2013 | Musallam et al. |
| 2016/0123921 | A1* | 5/2016 | Li .................. G01N 27/416 324/439 |

OTHER PUBLICATIONS

PCT Written Opinion for PCT Counterpart Application No. PCT/SG2016/050115, 4 pgs. (dated Apr. 27, 2016).

PCT International Preliminary Report on Patentability for PCT Application No. PCT/SG2016/050115, 7 pgs. (dated Feb. 1, 2017).

Matt Duwe, et al., "Low power integrated potentiostat design for electrodes with improved accuracy," 2011 IEEE 54th International Midwest Symposium on Circuits and Systems (MWSCAS), pp. 1-4 (Aug. 10, 2011).

"Introduction to Switched-Capacitor Circuits," Sep. 3, 2013 [Retrieved on Apr. 22, 2016 from http://web.archive.org/web/20130101000000*/http://www.seas.ucla.edu/brweb/teaching/AIC_Ch12.pdf; for the purpose of establishing publication date of this citation].

Christian C. Enz, et al., "Circuit techniques for reducing the effects of op-amp imperfections: autozeroing, correlated double sampling, and chopper stabilization," Proceeding of the IEEE, vol. 84, No. 11, pp. 1584-1614 (Nov. 30, 1996).

Jichun Zhang, et al., "Electrochemical array microsystem with integrated potentiostat," 2005 IEEE Sensors, pp. 385-388 (Nov. 3, 2005).

J.P. Villagrasa, et al., Chapter 10: Bioelectronics for amperometric Biosensors. State of the Art in Biosensors—General Aspects, pp. 241-274 (Mar. 13, 2013).

Ahmadi, el al., "A Very Low Power CMOS Potentiostat for Bioimplantable Applications," IDEAS, 2005, 6 pgs, IEEE Computer Society, Canada.

Duwe, et al., "Offset Correction of Low Power, High Precision Op Amp Using Digital Assist for Biomedical Applications," ISCAS, 2012, pp. 850-853, IEEE.

Kern, et at, "A Low-Power, Offset-Corrected Potentiostat for Chemical Imaging Applications," LASCAS, 2013, 4 pgs.

Kim, et al., "An 0.18μm CMOS Electrochemical Sensor Readout IC for Exhaust Gas Monitoring," Prime, 2009, 4 pgs.

Kim. et al., "A CMOS Analog Front-End Interface IC for Gas Sensors," CASME, 2010, 4 pgs., IEEE.

Martin, et al., "A Low-Voltage, Chemical Sensor Interface for Systems-On-Chip: The Fully-Differential Potentiostat," ISCAS, 2004, pp. 892-895, IEEE.

Srinivasan, et al., "A Precision CMOS Amplifier Using Floating-Gates for Offset Cancellation," Custom Integrated Circuits Conference, 2007, pp. 739-742, IEEE JSSC.

* cited by examiner

METHOD AND CIRCUIT FOR PROVIDING AN ACCURATE VOLTAGE FOR ELECTROCHEMICAL SENSING

CROSS-REFERENCE TO RELATED APPLICATIONS

This patent application is a U.S. National Phase Application under 35 U.S.C. § 371 of International Application No. PCT/SG2016/050115, filed on Mar. 11, 2016, entitled METHOD AND CIRCUIT FOR PROVIDING ACCURATE VOLTAGE FOR ELECTROMECHANICAL SENSING, which claims priority from Singapore Patent Application No. 10201501871U, filed Mar. 11, 2015.

TECHNICAL FIELD

The present invention generally relates to methods and circuits for accurately controlling potentials, and more particularly relates to a method and circuit to accurately control potentials in a potentiostat circuit for electrochemical sensing.

BACKGROUND OF THE DISCLOSURE

A three-electrode potentiostat is a widely-used electronic circuit used in sensor devices to analyze electrochemical and biochemical cells in the chemical industry, health industry and biology industry. The three-electrode potentiostat controls potentials of two electrodes and senses the current flowing through a third electrode. Depending on the applied potential difference across the two electrodes and the concentration of the electrochemical cell, a certain amount of cell current sinks into and/or out of the third electrode. Since the output current is very small (such as tens of nanoamperes or less) and the offset voltage may cancel out the small amount of current, the offset needs to be very small.

Moreover, for a large biosensor array including several potentiostats in a one microchip, the offset variation between the potentiostats tends to deteriorate the sensing accuracy. Thus, the offset variation needs to be tiny.

Conventional potential control schemes for potential deviation suppression are costly and time consuming and may fall within one of three conventional methods: a floating-date transistor method, a back-gate tuning method and a correlated double sampling method. The floating-date transistor method and the back-gate tuning method are expensive, have high silicon area requirements and are time consuming. The correlated double sampling method disadvantageously generates a large potential swing.

Thus, what is needed is a quick, inexpensive method for accurately controlling potentials in a potentiostat circuit which at least partially overcomes the drawbacks of present approaches and provides improved silicon real estate requirements, time consumption and reduced potential swing. Furthermore, other desirable features and characteristics will become apparent from the subsequent detailed description and the appended claims, taken in conjunction with the accompanying drawings and this background of the disclosure.

SUMMARY

According to at least one embodiment of the present invention a method for controlling a potentiostat control loop circuit to provide an accurate cell voltage for electrochemically sensing a sample, wherein the cell voltage corresponds to a difference between electrode voltages at a first electrode and a second electrode of a three-electrode potentiostat is provided. The potentiostat control loop circuit includes a first amplifier having an output connected to a third electrode of the three-electrode potentiostat and a first input connected to a first potential. The circuit further includes a first switched capacitor network including a first capacitance device having a first electrode connected to a second input of the first amplifier, the first switched capacitor network also operatively connected to the first amplifier for operating in a first mode and a second mode to switchably couple the second input of the first amplifier to the second electrode of the three-electrode potentiostat. The method includes the step of, in the second mode, coupling the second input of the first amplifier to the second electrode of the three-electrode potentiostat via the first capacitance device by coupling a second electrode of the first capacitance device to the second electrode of the three-electrode potentiostat.

In accordance with another aspect of at least one embodiment of the present invention, a potentiostat control loop circuit for providing an accurate cell voltage to a three-electrode potentiostat for electrochemically sensing a sample coupled to the three-electrode potentiostat is provided. A first electrode of the three-electrode potentiostat is stabilized to a common mode voltage and the cell voltage is a difference between a voltage at the first electrode of the three-electrode potentiostat and a voltage at a second electrode of the three-electrode potentiostat. The circuit includes a first amplifier having an output connected to a third electrode of the three-electrode potentiostat and a first input connected to the common mode voltage and a first switched capacitor network coupled between a first node and a second input of the first amplifier. The first switched capacitor network includes a first capacitance device having a first electrode connected to the second input of the first amplifier and a second electrode switchably connectable to either the first node when a first switch of the first switched capacitor network is closed or to the common mode voltage when a second switch of the first switched capacitor network is closed. The second input of the first amplifier is connected to the first node by a third switch of the first switched capacitor network. The first switched capacitor network is operatively controlled to open the first switch while closing the second and third switches and, alternatively, closing the first switch when opening the second and third switches. The first node is also coupled to the second electrode of the three-electrode potentiostat.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present embodiment.

FIG. 1, comprising

FIG. 4, comprising FIGS. 4A, 4B and 4C, illustrates a control loop for a potentiostat circuit in accordance with a second embodiment, wherein FIG. 4A illustrates the control loop in accordance with the second embodiment, FIG. 4B illustrates the control loop in accordance with the second embodiment in a clock phase ø1 and FIG. 4C illustrates the control loop in accordance with the second embodiment clock phase ø2.

Skilled artisans will appreciate that elements in the figures are illustrated for simplicity and clarity and have not necessarily been depicted to scale.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of the present embodiments to present methods to control potentials accurately in three electrode potentiostats in electrochemical sensor devices such as those used in the chemical industry, health industry and biology industry. By employing a proposed switched capacitor network, control loops for the three electrode potentiostat provide stable voltage differences between the reference electrode and the working electrode without a large voltage swing. Since the methods in accordance with the present embodiments require only a few switches and a few capacitors, they are not only less costly in silicon area but also have less power consumption than conventional methods. The methods in accordance with the present embodiments also have quick calibration and no large potential swings because they exclude large time-constant electrochemical or biochemical cells when offset sampling. By employing a proposed switched capacitor network with a conventional potentiostat, control loops in accordance with the present embodiments provide nearly ideal voltages by cheaper and quicker processing using a low power supply. Gain error is also calibrated in accordance with the present embodiments.

Figure 1A:
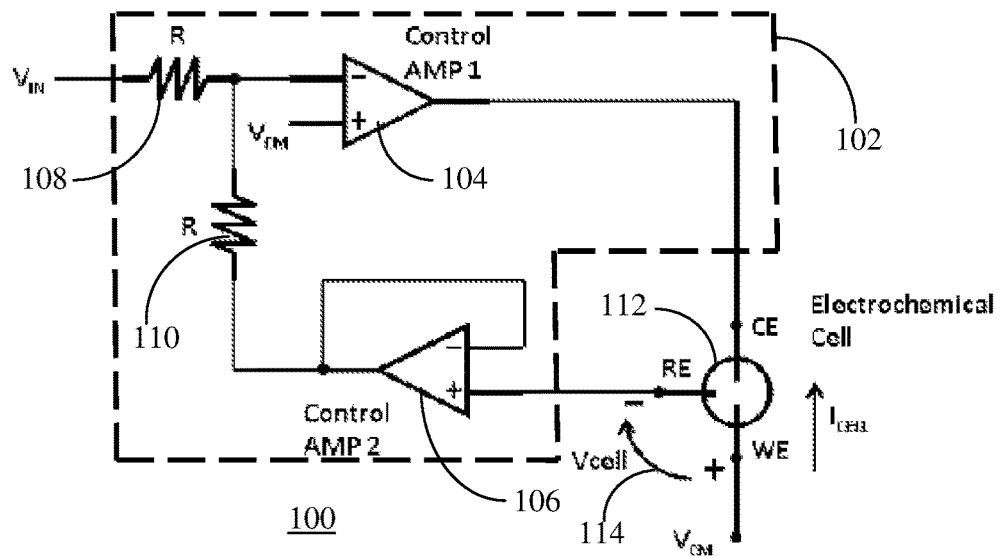
FIGS. 1A and 1B, illustrates circuit diagrams of control loops for conventional potentiostat circuits.

Referring to FIG. 1A, a circuit diagram 100 of a typical configuration of a conventional potentiostat control loop circuit is depicted. A control loop circuit 102 is configured by two amplifiers 104, 106 and a front-end resistive ladder comprising resistors 108, 110. Connecting the two control amplifiers 104, 106 with the frontend resistors 108, 110 forms a feedback configuration coupled to a counter electrode (CE) and a reference electrode (RE) of a three-electrode potentiostat 112 to control the cell potential of the three-electrode potentiostat 112 in order for the three-electrode potentiostat 112 to act as an electrochemical cell for electrochemically sensing a sample in the electrochemical cell. A trans-impedance amplifier also forces a potential of a working electrode (WE) of the potentiostat/electrochemical cell 112 to a common-mode voltage ($V_{CM}$). This circuit configuration forces the voltage difference of the externally applied $V_{IN}$ and $V_{CM}$ to the cell potential between WE and RE, which is Vcell 114.

Vcell 114 is a first order approximation with an assumption that there are no non-idealities on the amplifiers 104, 106. The non-idealities on the operational amplifiers 104, 106, however, deviate the cell potential Vcell 114 from ideal values. Assuming a gain ($A_x$) and an input-referred offset ($V_{os,x}$) of the control amplifier x, the cell voltage Vcell 114 is approximated by Equation (1) as follows:

$$V\text{cell} \approx (1-\Delta_{err}) \times (V_{IN} - V_{CM}) + (1-\Delta_{err}) \times V_{off,total} \quad (1)$$

where $\Delta \equiv 1/A$, $A \equiv A_1 \equiv A_2$, and $V_{off}$.

While the gain error $\Delta_{err}$ can be nearly cancelled by 60 dB of amplifier gain, offset voltages have a direct effect on the potential deviation. Typically, an operational amplifier has several millivolts to several tens of millivolts of offset voltage. Accordingly, the total offset voltage is typically more than ten millivolts.

Figure 1B:
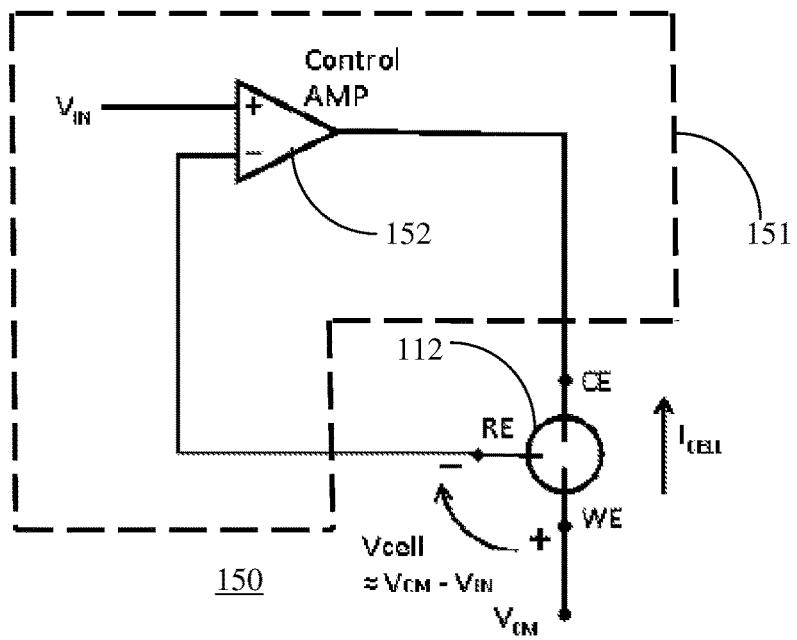

Another configuration of a conventional control loop circuit 151 for a potentiostat 112 which is widely used nowadays is depicted in a circuit diagram 150 in FIG. 1B. It includes only one amplifier 152 that forces the potential of the reference electrode (RE) to $V_{IN}$. Assuming the non-idealities (gain A and offset voltage $V_{off}$) of the amplifier 152, the cell voltage Vcell 154 is approximated by Equation (2) as follows:

$$V\text{cell} \approx (1-\Delta_{err}) \times (V_{CM} - V_{IN}) + (1-\Delta_{err}) \times V_{off} \quad (2)$$

where $\Delta_{err} \equiv 1/A$. The control loop 151 also has a direct effect of offsetting the potential deviation.

A straightforward way to reduce operational amplifier offset is to employ large transistors in the design. This technique, however, requires larger silicon area and additional power consumption. Two types of conventional tuning techniques for a specific node voltage of a transistor include a floating gate technique and a p-channel metal oxide semiconductor (PMOS) field effect transistor (FET) back gate technique. The floating gate technique utilizes floating gate transistors in critical pair transistors to be able to reduce the offset induced from the threshold mismatch of the transistors. However, fabricating such devices requires additional process steps which lead to additional fabrication cost.

The PMOS FET back-gate technique tunes a node voltage by a feedback system which uses the back-gates of PMOS FETs to sense offset and successively adjust the tuning voltage. An analog feedback system includes three or more additional operational amplifiers and offset storage capacitors and a mixed mode feedback system includes a comparator, a capacitive voltage incrementer and a large-scaled digital circuit. Thus, either expensive analog circuits (including operational amplifiers) or complex digital circuits are required for such feedback systems.

Another feedback technique uses a filter and a voltage-controlled current-source which are applied fed back to an operational amplifier to compensate the offset. This technique tunes an analog current thus requiring highly accurate analog circuits, including operational amplifiers and resistors, thereby requiring more cost. A further technique using a Zener diode has been proposed to create stable input voltages to the potentiostat. While simple to implement, this Zener diode technique does not solve the problem caused by operational amplifier offset Another method to reduce the operational amplifier's offset is an auto-zero/correlated double sampling technique (CDS). By means of double sampling, this method can effectively reduce the offsets. However, if the correlated double sampling is applied to the constituent operational amplifiers in the potentiostat circuit, the cell potential Vcell has a large droop in the compensation phase because of the leakage current in the feedback. Vcell also has a large voltage swing when it changes to an offset-sampling mode.

Figure 2:
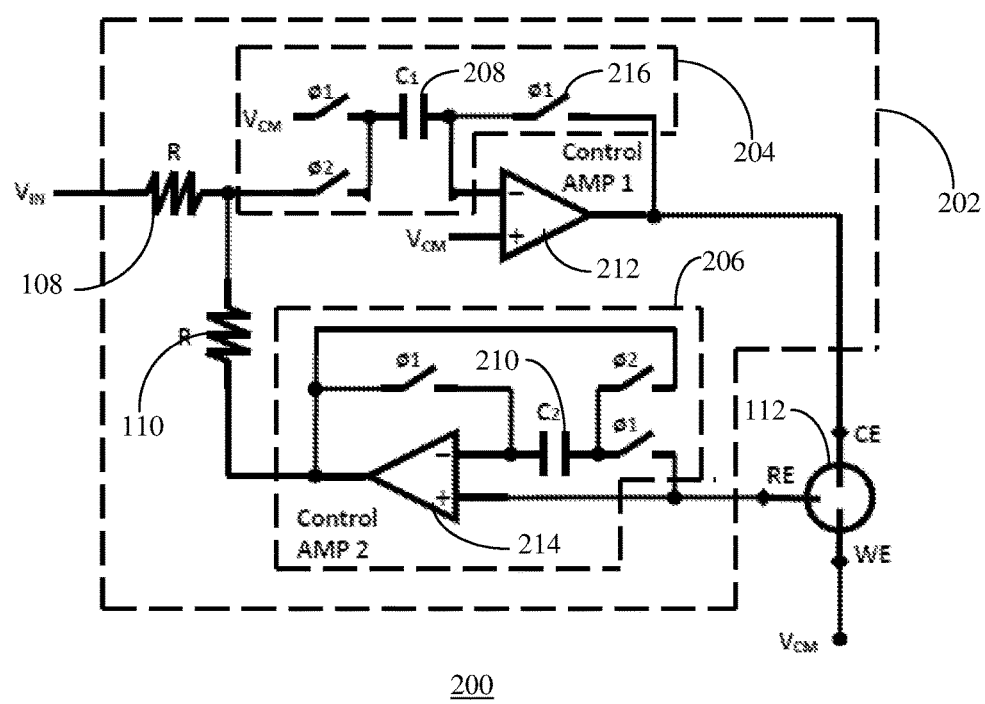
FIG. 2 illustrates a circuit diagram of a potentiostat control loop using a conventional auto-zero correlated double sampling (CDS) technique.

Referring to FIG. 2, a circuit diagram 200 depicts a potentiostat control loop circuit 202 using a conventional auto-zero correlated double sampling (CDS) technique. Switched capacitor networks 204, 206 synchronize with non-overlapping clocks, ø1 and ø2. During clock phase ø1 (an offset sampling mode), the network capacitance devices, C1 208 and C2 210, sample the offset voltages of control amplifiers 212, 214. The control amplifiers 212, 214 are preferably operational amplifiers and the capacitance devices 208, 210 are preferably capacitors. In the following clock phase ø2 (compensation mode), the control amplifiers' 212, 214 offsets are compensated by the sampled voltages.

Yet, just applying the CDS technique to the operational amplifiers 212, 214 has a problem: a leakage current of a feedback switch 216 of the control amplifier 212 causes a large droop in the voltage (i.e., a large drop in an efficiency) of the voltages during the compensation period.

Figure 3:
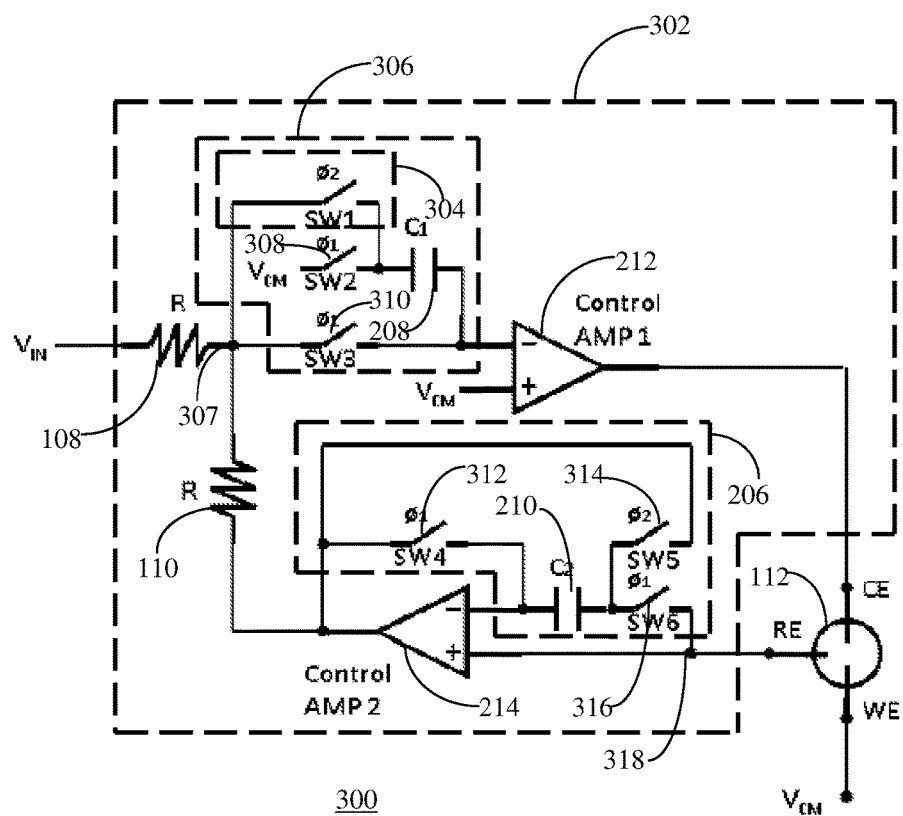
FIG. 3 illustrates a circuit diagram of a control loop for a potentiostat circuit in accordance with a first embodiment.

In accordance with a first embodiment, FIG. 3 depicts a circuit diagram 300 of a potentiostat control loop circuit 302 to address the drawbacks of the conventional CDS control loop 202 by using an outer feedback which includes the electrochemical cell and the control amplifier 214 during an offset sampling mode, instead of local feedback. The electrochemical cell 112 is coupled to a sample for electrochemically sensing the sample, the electrochemical cell being structured as a three-electrode potentiostat. A working electrode (WE) of the electrochemical cell 112 is connected to the common mode voltage ($V_{CM}$) for powering the electrochemical sensing. The switched capacitor network 306 is also connected to the common mode voltage and is coupled between a first node 307 and a non-inverted input of the amplifier 212. The switched capacitor network 306 includes switch 304, the capacitor 208, a switch 308 and a switch 310. The switches 308, 310 both close in a first operational mode when the switch 304 opens and, alternatively, in a second operational mode open when the switch 304 closes.

The switched capacitor network 206 includes a switch 312, a capacitor 210, a switch 314 and a switch 316. The switches 312, 316 both close in the first operational mode when the switch 314 and the switch 304 open and, alternatively, in the second operational mode while the switch 304 closes, the switches 312, 316 both open and the switch 314 closes. The switched capacitor network 206 is connected to a non-inverted input, an inverted input and an output of the control amplifier 214 and a second node 318. The second node 318 is connected to the reference electrode (RE) of the electrochemical cell 112. The counter electrode (CE) of the electrochemical cell 112 is connected to an output of the control amplifier 212.

The control loop 302 in accordance with the first embodiment provides a nearly constant cell voltage during the cancellation mode, yet has a large voltage swing when switched to the offset sampling mode. Some electrochemical cells, (e.g., glucose) require constant cell potential for a long time in order to place the cell in a stable condition. However, the switched capacitor networks 206, 306 need a periodical double sampling because of its unavoidable droop.

Figure 4A:
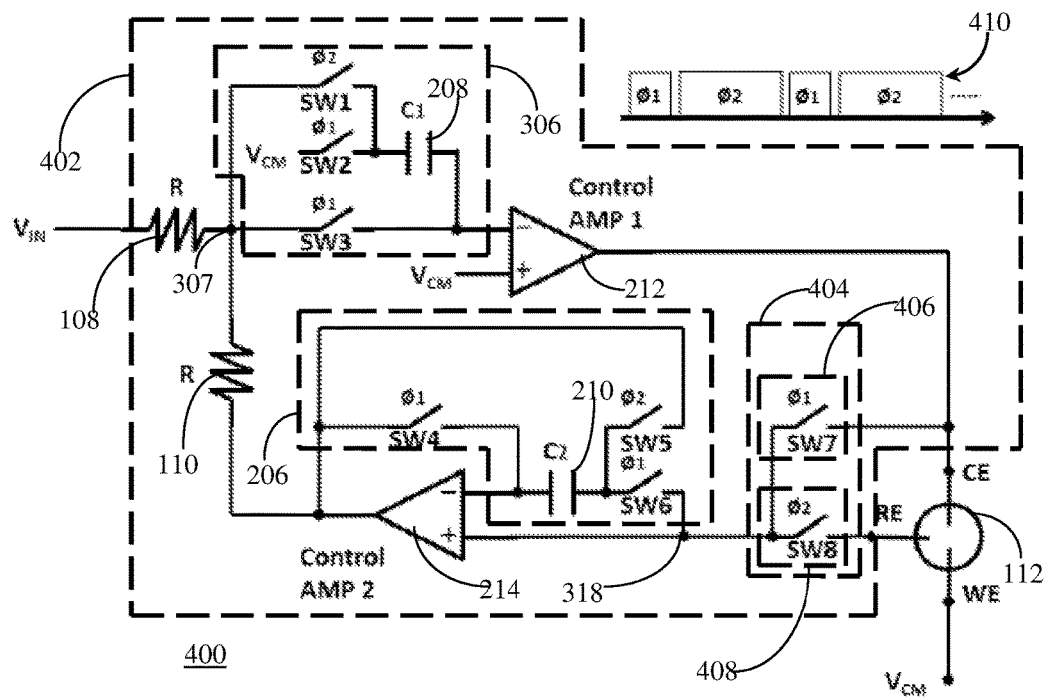

Referring to FIG. 4A, a circuit diagram 400 depicts a potentiostat control loop circuit 402 in accordance with a second embodiment. The control loop circuit includes a switch pair 404 which includes a first switch 406 and a second switch 408. The switch pair 404 is operatively coupled to the switched capacitor network 206 and the switched capacitor network 306 to open and close the switches 406, 408 during the clock phases ø1 and ø2, respectively. In order to avoid the large swing of the cell voltage during the offset sampling clock phase ø1, the first switch 406 closes to disconnect the reference electrode of the electrochemical cell from the control loop and, alternately, connect the reference electrode of the electrochemical cell to the control loop for a longer compensation time duration during the compensation clock phase ø2 as depicted in a timing diagram 410. The timing diagram 410 depicts switching of the clock phases ø1 and ø2 in accordance with the second embodiment. Since the control amplifiers 212, 214 need to be in the feedback loop and the electrochemical cell does not necessarily reset to the initial non-compensated Q-point in the offset sampling mode, closing the first switch 406 while opening the second switch 408 during the clock phase ø1 excludes the electrochemical cell from the control loop 402 during the offset sampling mode (i.e., clock phase ø1).

Figure 4B:
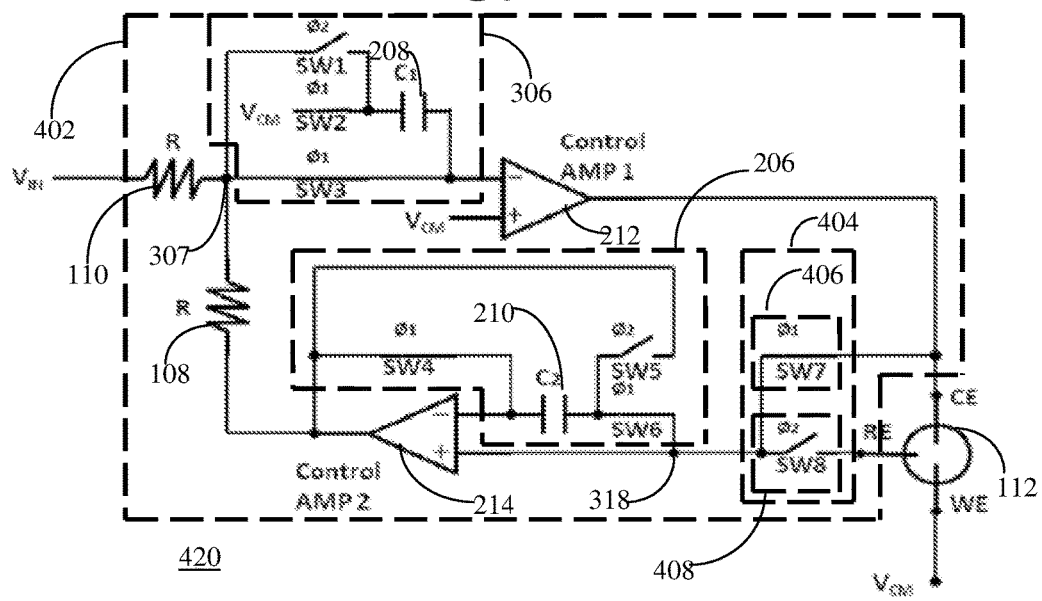
Figure 4C:
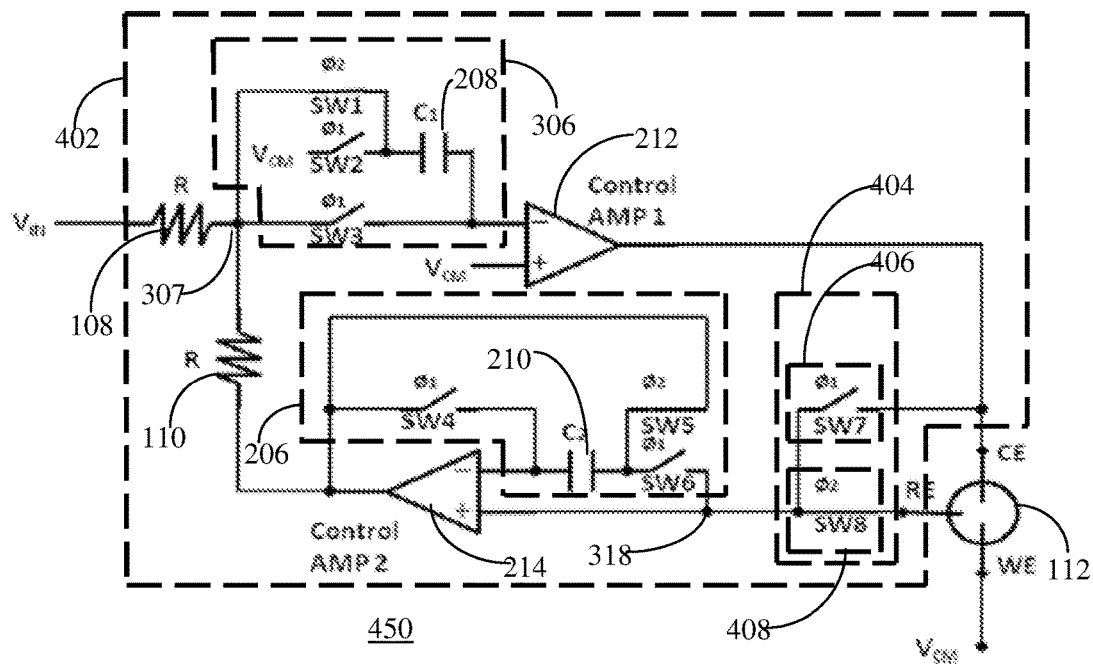

Referring to FIGS. 4B and 4C, circuit diagrams 420, 450 depict the control loop circuit 402 during the clock phases ø1 and ø2, respectively. Referring to the circuit diagram 420 (FIG. 4B), during the clock phase ø1, the network capacitors 208, 210 sample the offset voltages of control amplifiers 212, 214, respectively. As mentioned above, closing the switch 406 while opening the second switch 408 during the clock phase ø1 excludes the electrochemical cell from the control loop 402 during the offset sampling mode. Referring to the circuit diagram 450 (FIG. 4C), during the clock phase ø2, the network capacitor 208 is connected to the first node 307, a conjunction node of the front-end resistors 108, 110 of the resistor ladder, forcing the first node 307 potential nearly to the common-mode voltage ($V_{CM}$). On the other hand, the network capacitor 210 is included in the feedback of the control amplifier 214 to cancel the offset of the amplifier 214. The switch 406 is open and the switch 408 is closed to form a normal feedback configuration with the electrochemical cell.

Figure 5:
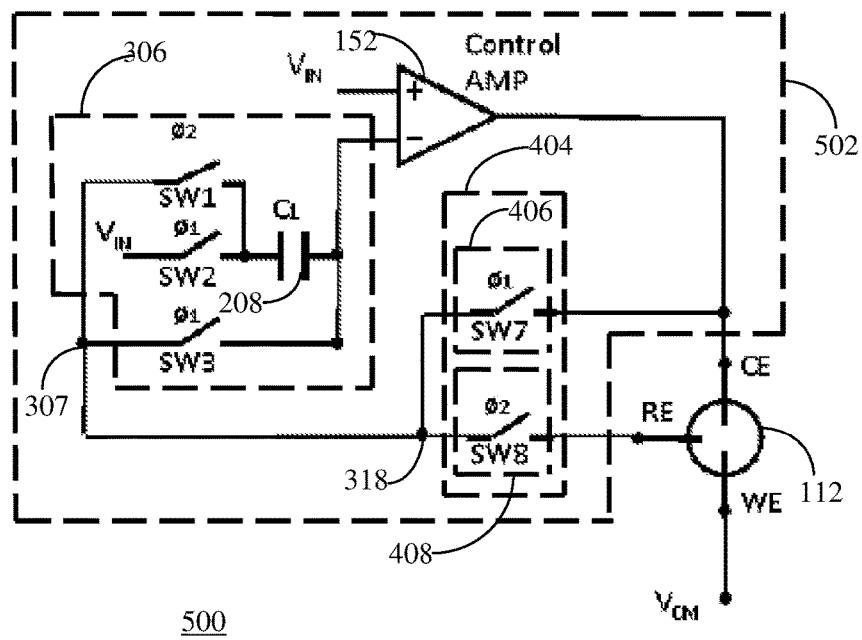
FIG. 5 illustrates a circuit diagram of a control loop for a potentiostat circuit in accordance with a third embodiment.

Referring to FIG. 5, a circuit diagram 500 depicts a control loop circuit 502 for a potentiostat circuit in accordance with a third embodiment which employs the switched capacitor network 306 to a one amplifier 152 control loop configuration such as the control loop circuit 150 (FIG. 1B). In the control loop circuit 502, the first node 307 is directly connected to the second node 318. The function of the control loop circuit 502 in both clock phases ø1 and ø2 is similar to the operation of the control loop circuit 402 (FIGS. 4B, 4C) as shown in the timing diagram 410.

Figure 6:
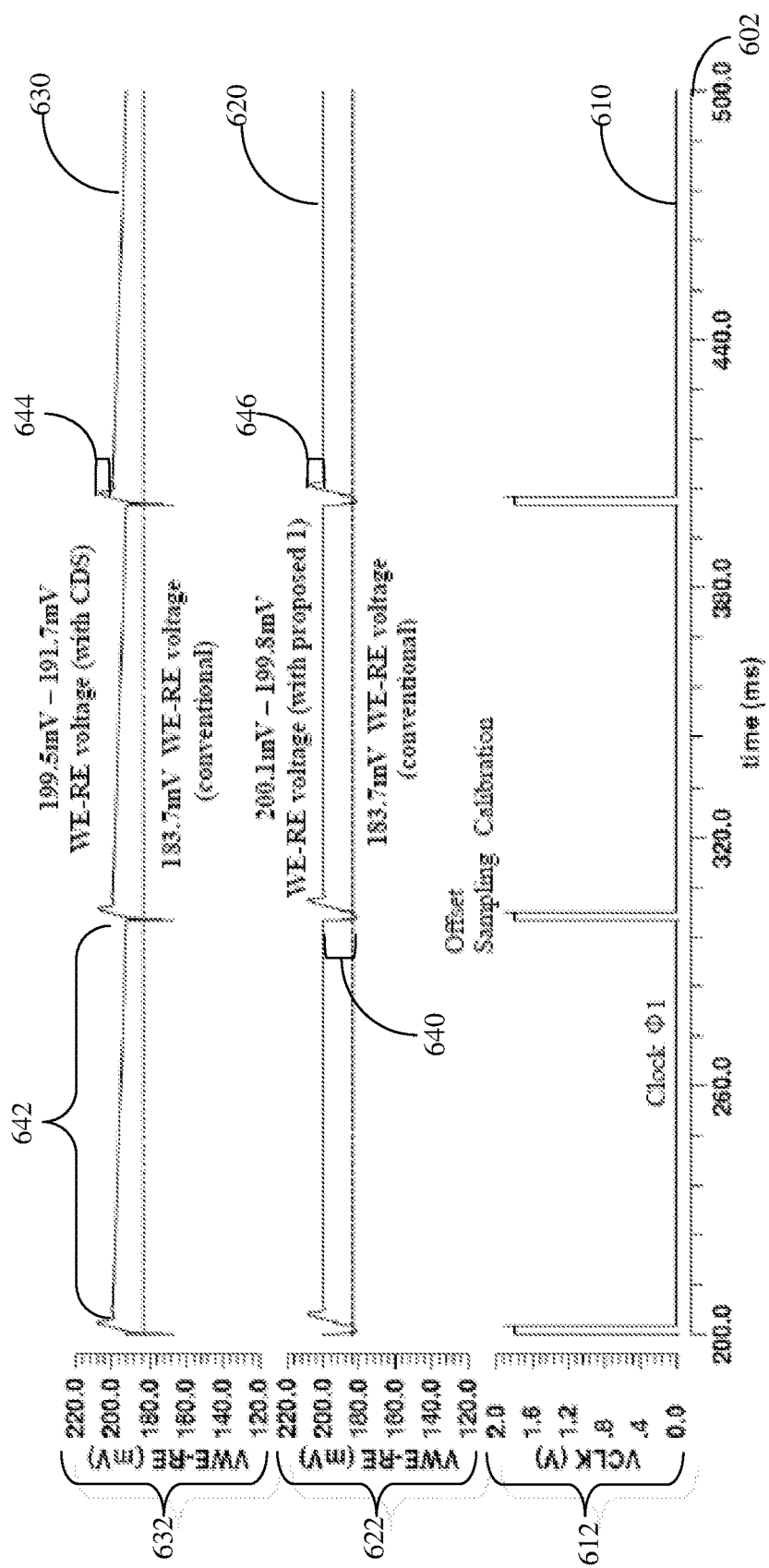
FIG. 6 illustrates a graph of simulation results of the operation of the control loop for the potentiostat circuit in accordance with the first embodiment.

FIG. 6 illustrates a graph 600 of simulation results using 0.18 μm complementary metal oxide semiconductor (CMOS) model parameters of the operation of the potentiostat control loop circuit 302 in accordance with the first embodiment. Time is plotted along a vertical axis 602. At the bottom of the graph 600, a timing trace 610 has voltage amplitude 612 plotted horizontally as $V_{CLK}$ in volts. In the middle of the graph 600, the cell potential 620 (which is the working electrode (WE) to reference electrode (RE) voltage difference ($V_{WE-RE}$) 622) in millivolts during the simulation is plotted for operation in accordance with the first embodiment and can be compared to a cell potential 630 of simulation results of the working electrode to reference electrode voltage ($V_{WE-RE}$) 632 in accordance with a conventional auto-zero correlated double sampling (CDS) technique.

In the simulation depicted in the graph 600, DC gains of the control amplifiers 212, 214 are set to 70 dB and offset voltages of the control amplifiers 212, 214 are assumed to be 5 mV and 6 mV, respectively. The input voltage $V_{IN}$ is set to 0.6V and the common-mode voltage $V_{CM}$ is set to 0.4V. Without the calibration, the cell potential 620 has an offset 640 of 16.3 mV, which is similar to the theoretical value of $V_{off\ total}$ of 16 mV calculated in Equation (1). When using a conventional CDS technique, the cell voltage 630 has a large droop from 199.5 mV to 191.7 mV during the calibration mode 642. At the end of the calibration mode 642, the offset 644 increases to 8.3 mV. On the other hand, operation of the potentiostat control loop circuit 302 in accordance with the first embodiment exhibits 199.8 mV voltage 620 in the clock phase ø2, which has a very small offset 646 of 0.2 mV as compared with the offset 644 during operation in accordance with the conventional CDS technique. Thus operation in accordance with the first embodiment advantageously reduces voltage droop in the calibration mode.

Figure 7:
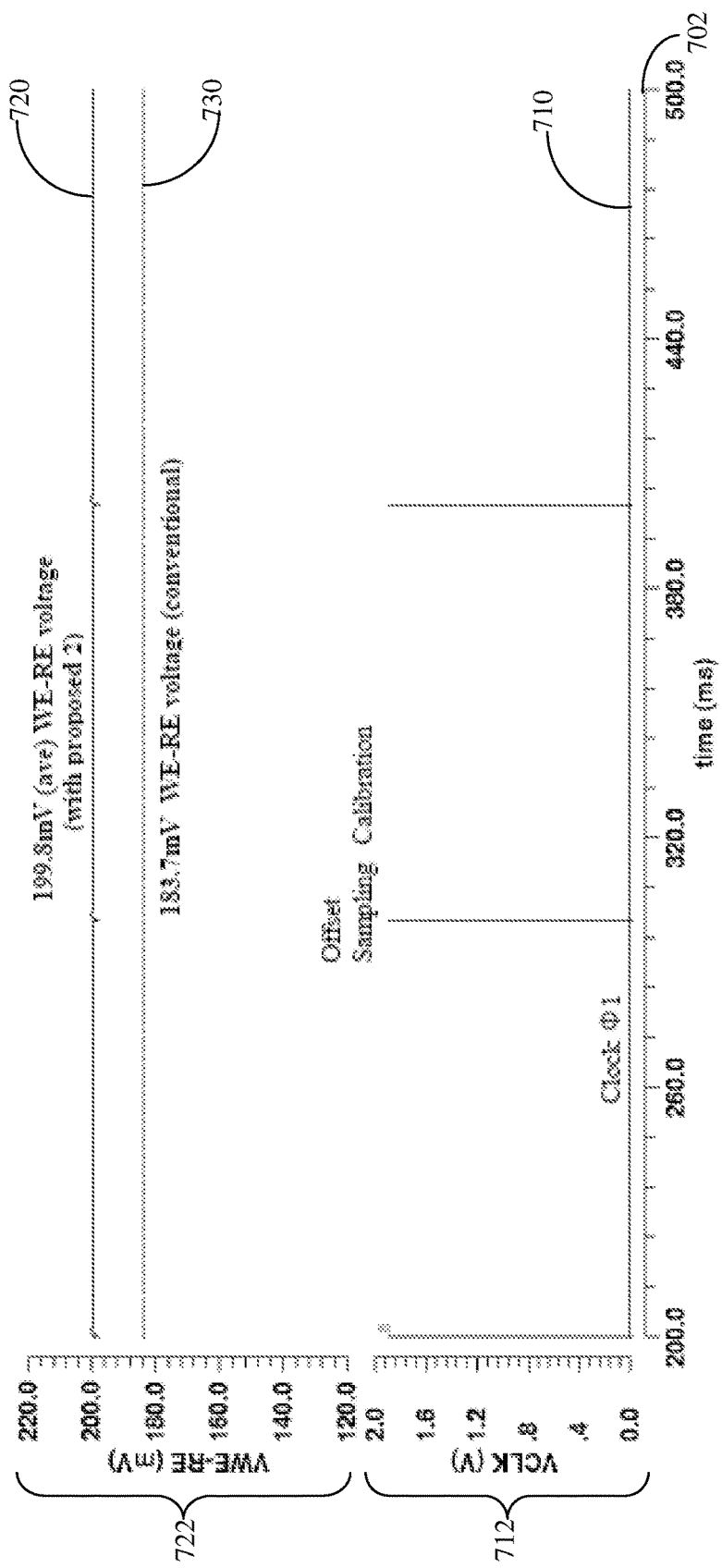
FIG. 7 illustrates a graph of simulation results of the operation of the control loop for the potentiostat circuit in accordance with the second embodiment.

FIG. 7 illustrates a graph 700 of simulation results of the operation of the potentiostat control loop circuit 402 in accordance with the second embodiment. Time is plotted along a vertical axis 702. At the bottom of the graph 700, a timing trace 710 has voltage amplitude 712 plotted horizontally as $V_{CLK}$ in volts. At the top of the graph 700, the cell potential 720 (which is $V_{WE-RE}$ 722 in millivolts) during the simulation is plotted for operation in accordance with the first embodiment and can be compared to a cell potential 730 of simulation results of the $V_{WE-RE}$ 722 in accordance with a CDS technique.

From the graph 700, it can be seen that although this simulation uses the same circuit non-idealities as the simulation depicted in the graph 600, the cell voltage does not have a large voltage swing in clock phase ø1. The average voltage in ø2 is 199.8 mV and the glitch in clock phase ø1 is advantageously very small while the peak voltage is 197.4 mV, thereby showing the effectiveness of operation in accordance with the second embodiment in reducing the voltage deviation from an ideal voltage (i.e., 200 mV).

Figure 8:
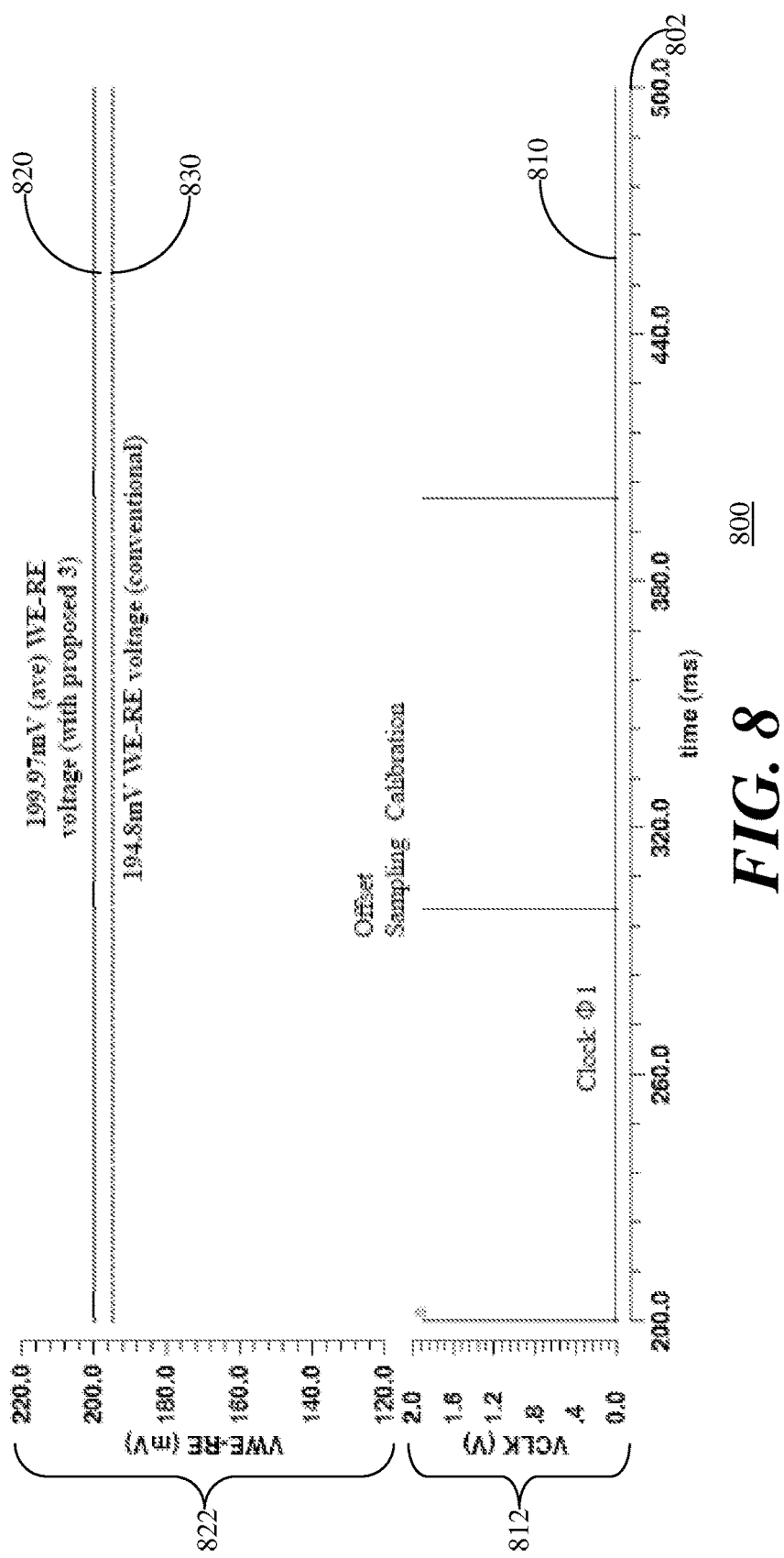
FIG. 8 illustrates a graph of simulation results of the operation of the control loop for the potentiostat circuit in accordance with the third embodiment.

FIG. 8 illustrates a graph 800 of simulation results of the operation of the potentiostat control loop circuit 502 in accordance with the third embodiment. Time is plotted along a vertical axis 802. At the bottom of the graph 800, a timing trace 810 has voltage amplitude 812 plotted horizontally as $V_{CLK}$ in volts. At the top of the graph 800, the cell potential 820 (which is $V_{WE-RE}$ 822 in millivolts) during the simulation is plotted for operation in accordance with the first embodiment and can be compared to a cell potential 830 of simulation results of the $V_{WE-RE}$ 822 in accordance with a CDS technique. The average voltage 820 in ø2 in accordance with the third embodiment is 199.97 mV, while the average voltage 830 is 194.8 mV in operation of the conventional circuit 151 without the switched capacitor network 306 (FIG. 5).

Using an alternative path during the offset sampling mode (phase ø1) by operation of the switches 406, 408 reduces voltage swing of the cell voltage and implementing the switched capacitor networks 206, 306 bring the cell voltage very close to an ideal voltage, while making the potentiostat control loop circuits 302, 402, 502 scalable for semiconductor electrochemical sensor applications, providing robust solutions where highly accurate voltages must be provided to the electrochemical cell for the electrochemical sensing. Such potentiostat control loop circuits can find applications in other potentiostat circuit applications where low cost and accuracy are requirements.

Thus it can be seen that the present embodiments 302, 402, 502 provide a quick, inexpensive method and circuits for accurately controlling potentials in a potentiostat circuit which provides improved silicon real estate requirements, time consumption and reduced potential swing and an electrochemical cell with an accurate voltage. The potentiostat control loop circuits 302, 402, 502 in accordance with the present embodiments require only switch and capacitor networks without any complex/active circuit blocks. Therefore, the potentiostat control loop circuits 302, 402, 502 in accordance with the present embodiments are easy to implement. Operation in accordance with the present embodiments can advantageously reduce voltage deviation to 0.2 mV average with a small glitch of 2.6 mV, while the deviation is 16.3 mV without any compensation methods for two amplifiers in the control loop. In addition, the potentiostat control loop circuits 302, 402, 502 in accordance with the present embodiments provides concurrent calibration and low power supply architectures and operation of the potentiostat control loop circuits 302, 402, 502 provides increased performance, faster calibration time, smaller silicon area requirements and more accurate controlled potentials for longer times than conventonal potentiostat control loop circuits.

While exemplary embodiments have been presented in the foregoing detailed description of the invention, it should be appreciated that a vast number of variations exist. It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of elements and method of operation described in an exemplary embodiment without departing from the scope of the invention as set forth in the appended claims.

What is claimed is:

1. A potentiostat control loop circuit comprising:
   a three-electrode potentiostat having a first electrode, a second electrode and a third electrode, wherein the first electrode is stabilized to a common mode voltage;
   a first control amplifier having an output connected to the third electrode of the three-electrode potentiostat and a first input connected to a first potential, the first control amplifier to provide a cell voltage to the three-electrode potentiostat, wherein the cell voltage comprises a difference between a voltage at the first electrode of the three-electrode potentiostat and a voltage at the second electrode of the three-electrode potentiostat; and
   a first switched capacitor network coupled between a first node and a second input of the first control amplifier; wherein the first switched capacitor network comprises a first capacitance device having a first electrode connected to the second input of the first control amplifier and a second electrode switchably connectable to either the first node when a first switch of the first switched capacitor network is closed or to the first potential when a second switch of the first switched capacitor network is closed, the second input of the first control amplifier being connected to the first node by a third switch of the first switched capacitor network and the first switched capacitor network operatively controlled to open the first switch while closing the second and third switches and, alternatively, closing the first switch when opening the second and third switches, wherein the first node is coupled to the second electrode of the three-electrode potentiostat.

2. The potentiostat control loop circuit in accordance with claim 1 further comprising a switch pair having first ends of first and second switches connected to a second node, a second end of the first switch connected to the third electrode of the three-electrode potentiostat, and a second end of the second switch connected to the second electrode of the three-electrode potentiostat to form a switchable feedback configuration with the three-electrode potentiostat, wherein the switch pair is operatively coupled to the first switched capacitor network such that the first switch of the switch pair is closed and the second switch of the switch pair is open when the first switch of the first switched capacitor network is open and the second and third switches of the first switched capacitor network are closed and, alternatively, the first switch of the switch pair is open and the second switch of the switch pair is closed when the first switch of the first switched capacitor network is closed and the second and third switches of the first switched capacitor network are open.

3. The potentiostat control loop circuit in accordance with claim 2 wherein the first node is directly connected to the second node.

4. The potentiostat control loop circuit in accordance with claim 1 wherein the first potential is an input voltage.

5. The potentiostat control loop circuit in accordance with claim 1 wherein the first potential is a common mode voltage and a second potential coupled to the first node is an input voltage.

6. The potentiostat control loop circuit in accordance with claim 5 further comprising:
a second control amplifier having a first input connected to the second node and an output coupled to the first node; and
a second switched capacitor network connected to the first input, a second input and the output of the second control amplifier and comprising a second capacitor and a first switch, a second switch and a third switch, the second switched capacitor network operatively coupled to the first switched capacitor network such that the first and third switches of the second switched capacitor network are closed and the second switch of the second switched capacitor network is open when the first switch of the first switched capacitor network is open and the second and third switches of the first switched capacitor network are closed and, alternatively, the first and third switches of the second switched capacitor network are open and the second switch of the second switched capacitor network is closed when the first switch of the first switched capacitor network is closed and the second and third switches of the first switched capacitor network are open.

7. The potentiostat control loop circuit in accordance with claim 6 further comprising a resistor ladder including a first resistor connected between the input voltage and the first node and a second resistor connected between the first node and the output of the second control amplifier.

8. The potentiostat control loop circuit in accordance with claim 6 wherein the second capacitance device is a network capacitor.

9. The potentiostat control loop circuit in accordance with claim 6 wherein the second control amplifier is an operational amplifier and wherein the first input of the second control amplifier is a non-inverted input and the second input of the first control amplifier is an inverted input.

10. The potentiostat control loop circuit in accordance with claim 1 wherein the first capacitance device is a network capacitor.

11. The potentiostat control loop circuit in accordance with claim 1 wherein the first control amplifier is an operational amplifier and wherein the first input of the first control amplifier is a non-inverted input and the second input of the first control amplifier is an inverted input.

12. The potentiostat control loop circuit in accordance with claim 1 wherein the first electrode of the three-electrode potentiostat is a working electrode, a second electrode of the three-electrode potentiostat is a reference electrode and a third electrode of the three-electrode potentiostat is a counter electrode.

* * * * *